US012779009B2

(12) United States Patent
Ghim et al.

(10) Patent No.: US 12,779,009 B2

(45) Date of Patent: Nov. 3, 2026

(54) PHARMACEUTICAL COMPOSITION FOR TREATING DRY EYE SYNDROME

(71) Applicant: Novacell Technology Inc., Pohang-si (KR)

(72) Inventors: Jae Wang Ghim, Pohang-si (KR); Tae Hoon Lee, Seoul (KR); Hyun Ju Lee, Seoul (KR)

(73) Assignee: Novacell Technology Inc., Seoul (KR)

( * ) Notice: Subject to any disclaimer, the term of this patent is extended or adjusted under 35 U.S.C. 154(b) by 952 days.

(21) Appl. No.: 17/999,911

(22) PCT Filed: Apr. 22, 2021

(86) PCT No.: PCT/KR2021/005118

§ 371 (c)(1),
(2) Date: Nov. 25, 2022

(87) PCT Pub. No.: WO2021/241892

PCT Pub. Date: Dec. 2, 2021

(65) Prior Publication Data

US 2023/0226137 A1 Jul. 20, 2023

(30) Foreign Application Priority Data

May 25, 2020 (KR) ........................ 10-2020-0062610

(51) Int. Cl.
*A61K 38/08* (2019.01)
*A61P 27/02* (2006.01)
*A61P 31/04* (2006.01)

(52) U.S. Cl.
CPC .............. *A61K 38/08* (2013.01); *A61P 27/02* (2018.01); *A61P 31/04* (2018.01)

(58) Field of Classification Search
None
See application file for complete search history.

(56) References Cited

U.S. PATENT DOCUMENTS

| | | | |
|---|---|---|---|
| 10,421,781 | B2 | 9/2019 | Lee et al. |
| 2010/0184696 | A1 | 7/2010 | O'Neil |
| 2011/0105416 | A1 | 5/2011 | Brandenburg |
| 2014/0256684 | A1 | 9/2014 | Beard et al. |

FOREIGN PATENT DOCUMENTS

| | | | |
|---|---|---|---|
| CN | 101155825 | A | 4/2008 |
| CN | 108473533 | A | 8/2018 |
| JP | 2019506362 | A | 3/2019 |
| KR | 1020040012929 | A | 2/2004 |
| KR | 1020140099526 | A | 8/2014 |
| KR | 1020160150548 | A | 12/2016 |
| KR | 1020170058498 | A | 5/2017 |
| KR | 101910908 | B1 | 10/2018 |

OTHER PUBLICATIONS

The Dry eye specialist (https://dryeyespecialist.com/neurotrophic-keratitis/> accessed Dec. 19, 2025) (Year: 2025).*
The American academy of Ophthalmology (https://www.aao.org/eye-health/diseases/what-is-fungal-keratitis> accessed Dec. 19, 2025) (Year: 2025).*
Extended European Search Report for European Application No. 21812573.0 dated Apr. 29, 2024.
Sosne, G et al., "Thymosin beta 4 ophthalmic solution for dry eye: a randomized, placebo-controlled, Phase II clinical trial conducted using the controlled adverse environment (CAE ™ ) model ", Clinical Ophthalmology, vol. 9, pp. 877-884 (2015).
Wessolowski, A.et al., "Antimicrobial activity of arginine- and tryptophan-rich hexapeptides: the effects of aromatic clusters, d-amino acid substitution and cyclization", J. Peptide Res., vol. 64, pp. 159-169 (2004).
International Search Report mailed Aug. 18, 2021, in International Application No. PCT/KR2021/005118.
Written Opinion mailed Aug. 18, 2021, in International Application No. PCT/KR2021/005118.
Aragona, P. et al., "Modern approach to the treatment of dry eye, a complex multifactorial disease: a P.I.C.A.S.S.O. board review," Br J Ophthalmol 105:446-453 (8 pages) (Jul. 2020).
Clayton, J., "Dry Eye," N Engl J Med 378:2212-23 (12 pages) (Jun. 2018).
Craig, J. et al., "TFOS DEWS II Definition and Classification Report," The Ocular Surface 15:276-283 (8 pages) (May 2017).
Harrell, C. et al., "The Molecular Mechanisms Responsible for Tear Hyperosmolarity-Induced Pathological Changes in the Eyes of Dry Eye Disease Patients," Cells 12:2755 (16 pages) (Dec. 2023).
Stevenson, W. et al., "Dry Eye Disease," Arch Ophthalmol. 130 (1):90-10 (11 pages) (Jan. 2012).
Tsubota, K. et al., "Defining Dry Eye from a Clinical Perspective," Int. J. Mol. Sci. 21:9271 (24 pages) (Dec. 2020).
Yamaguchi, T., "Inflammatory Response in Dry Eye," Invest Ophthalmol Vis Sci 59:DES192-DES199 (8 pages) (2018).
Zhang, X. et al., "Dry Eye Management: Targeting the Ocular Surface Microenvironment," Int. J. Mol. Sci. 18:1398 (28 pages) (Jun. 2017).

* cited by examiner

*Primary Examiner* — Tara L Martinez

(74) *Attorney, Agent, or Firm* — Potomac Law Group, PLLC; Judith Kim

(57) ABSTRACT

The present invention provides a novel pharmaceutical composition for treating dry eye syndrome. The composition significantly alleviates corneal damage and corneal opacity without side effects, thereby restoring damaged corneas and increasing tear secretion, and thus effectively treats ophthalmic diseases related to dry eye syndrome.

9 Claims, 4 Drawing Sheets

Specification includes a Sequence Listing.

PHARMACEUTICAL COMPOSITION FOR TREATING DRY EYE SYNDROME

REFERENCE TO SEQUENCE LISTING SUBMITTED ELECTRONICALLY

This application contains a sequence listing, which has been submitted electronically in ASCII format and is hereby incorporated by reference in its entirety. Said ASCII copy, created on Dec. 15, 2022, is named 4861-0001US01_sequence listing-new.txt, and is 2.68 KB in size.

TECHNICAL FIELD

The present invention relates to a novel pharmaceutical composition for treating dry eye syndrome, and more particularly, to a novel pharmaceutical composition for treating dry eye syndrome which can treat ophthalmic diseases related to dry eye syndrome without side effects.

BACKGROUND ART

Dry eye syndrome is a syndrome which generally causes symptoms such as foreign body sensation, burning sensation, or eye irritation due to a decrease in tear production or an increase in the loss of the tear film due to tear evaporation. Existing treatment for dry eye syndrome has focused on maintaining more than a certain amount of tears by conservative methods such as dropping an artificial lacrimal solution, which is an artificially made tear, or temporarily or permanently blocking tear ducts, in order to compensate for insufficient tears according to symptoms. However, such symptomatic treatment has insufficient effect and cannot directly remove the cause of disease. Therefore, in the recent treatment trend for dry eye syndrome, it is preferred that direct and ultimate treatment methods to relieve dry eye by reducing inflammation of the lacrimal glands and the eye's surface rather than passive treatment for symptom relief purposes. In addition, in moderate to severe dry eye syndrome which is difficult to be controlled with an artificial lacrimal solution, anti-inflammatory drugs such as cyclosporine, steroids, and autologous serum eye drops are used in combination as drugs for inflammation control rather than simple prescription of the artificial lacrimal solution. However, the artificial lacrimal solution has disadvantage that it should be used several times a day because the effect is temporary, and there is no protective effect against corneal damage, steroid preparations may cause fatal side effects such as glaucoma when used for a long period of time, and cyclosporine, a broad-spectrum immunosuppressant, also has limitations such as eye pain, burning sensation, foreign body sensation, and hyperemia, and some systemic side effects. In addition, contact lenses for treatment are inconvenient to use, and can provide the cause of infection, and the punctal occlusion procedure has disadvantage in that there is repulsion for surgery and it is difficult to restore the original state if side effects occur. Therefore, there is an urgent need to develop a preparation capable of effectively preventing or treating dry eye syndrome without side effects. In this regard, Korean Patent Publication No. 2014-0099526 discloses a use of cell-permeable peptide inhibitors of the JNK signal transduction pathway for the treatment of dry eye syndrome.

DISCLOSURE OF THE INVENTION

Technical Problem

The prior art, however, is likely to cause local irritation to the ocular-mucous membrane, is difficult to be administered in a predetermined dose, and thus may significantly reduce treatment efficiency.

An object of the present invention is to solve various limitations including the above limitations, and to provide a novel pharmaceutical composition for treating dry eye syndrome, which effectively treats dry eye syndrome by significantly inhibiting a decrease in the amount of tear secreted and a change in the shape of a cornea due to dry eye syndrome without side effects. However, the object is for illustrative purpose only and the scope of the present disclosure is not limited thereby.

Technical Solution

According to an aspect of the present invention, there is provided a pharmaceutical composition for treating and preventing dry eye syndrome, the composition containing, as an active ingredient, a peptide which has antibacterial activity and is composed of seven amino acids including an amino acid sequence selected from the group consisting of the following:

BOBWRYm, wherein, B is a basic amino acid each optionally selected from the group consisting of lysine (K) or arginine (R), and O is an aromatic amino acid each optionally selected from the group consisting of phenylalanine (F) or tryptophan (W).

According to another aspect of the present invention, there is provided a pharmaceutical composition for treating keratoconjunctivitis, the composition containing, as an active ingredient, a peptide which has antibacterial activity and is composed of seven amino acids including an amino acid sequence selected from the group consisting of the following:

BOBWRYm, wherein, B is a basic amino acid each optionally selected from the group consisting of lysine (K) or arginine (R), and O is an aromatic amino acid each optionally selected from the group consisting of phenylalanine (F) or tryptophan (W).

According to another an aspect of the present invention, there is provided a pharmaceutical composition for alleviating corneal damage and corneal opacity, the composition containing, as an active ingredient, a peptide which has antibacterial activity and is composed of seven amino acids including an amino acid sequence selected from the group consisting of the following:

BOBWRYm, wherein, B is a basic amino acid each optionally selected from the group consisting of lysine (K) or arginine (R), and O is an aromatic amino acid each optionally selected from the group consisting of phenylalanine (F) or tryptophan (W).

According to another aspect of the present invention, there is provided a method for treating dry eye syndrome in a subject, the method comprising administering the composition to the subject suffering from dry eye syndrome.

According to another aspect of the present invention, there is provided a use, in the production of a therapeutic agent for dry eye syndrome, of a peptide which has antibacterial activity and is composed of seven amino acids including an amino acid sequence selected from the group consisting of the following:

BOBWRYm, wherein, B is a basic amino acid each optionally selected from the group consisting of lysine (K) or arginine (R), and O is an aromatic amino acid each optionally selected from the group consisting of phenylalanine (F) or tryptophan (W).

Advantageous Effects

The novel pharmaceutical composition for treating dry eye syndrome of the present invention as described above remarkably suppresses a decrease in the amount of tear secreted due to dry eye syndrome and changes in keratoconjunctivitis and the shape of a cornea, thereby has an excellent effect of recovering a damaged cornea and increasing the amount of tear secreted, and thus can be utilized in the development of a safe and effective therapeutic agent for dry eye syndrome. However, the scope of the present invention is not limited by such an effect.

BEST MODE FOR CARRYING OUT THE INVENTION

Figure 1:
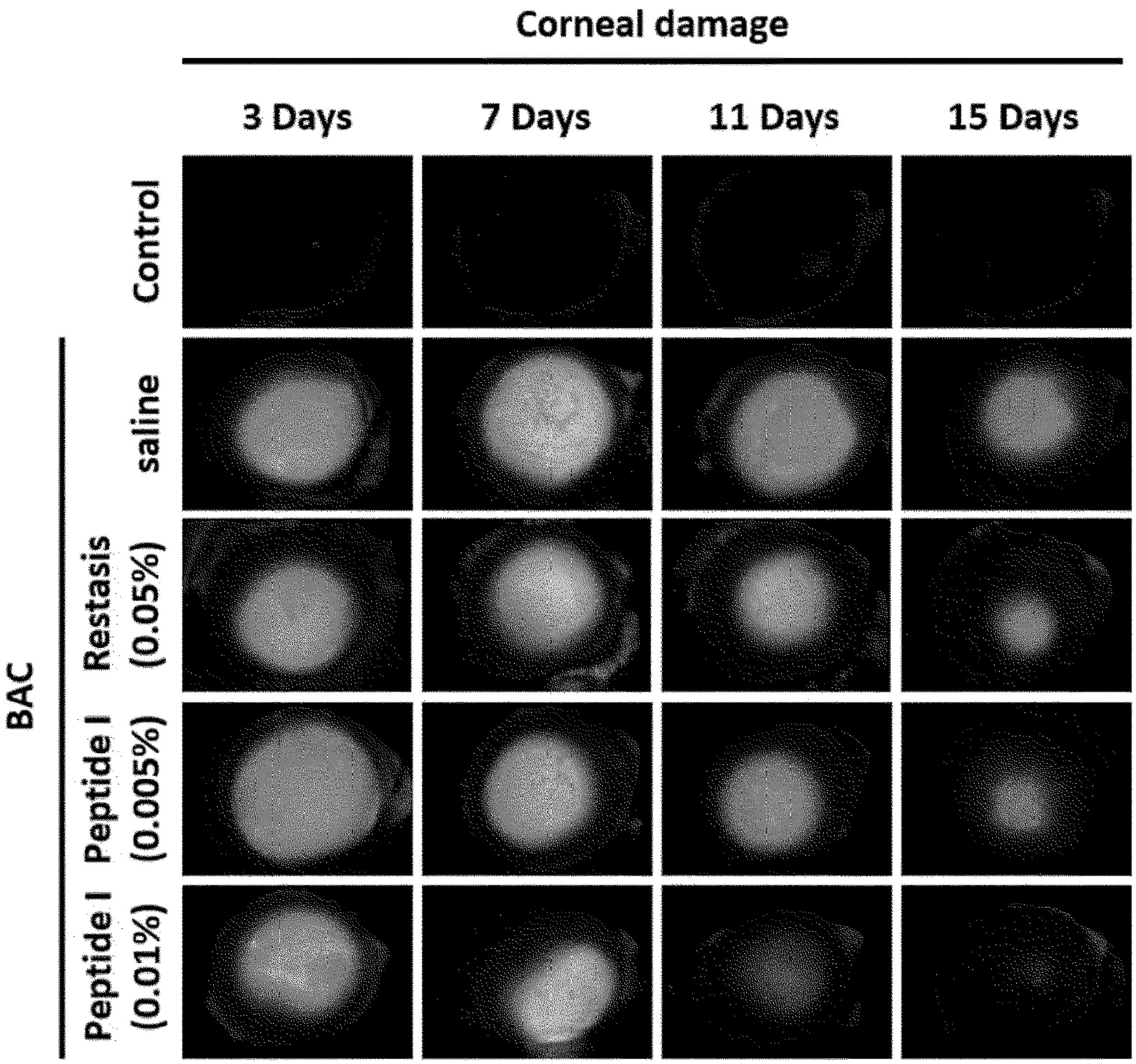
FIG. 1 shows images taken through a microscope and fluorescent staining of corneal damage by treating a peptide of the present invention to mouse models.

As used herein, the term "antibacterial peptide" refers to a cationic peptide compound which is generally composed of a relatively simple structure having a broad antibacterial spectrum against gram-positive bacteria, gram-negative bacteria, fungi, viruses, and the like, and although the mechanism of antibacterial peptides is not fully identified, it is generally known that the compound exhibits antibacterial activity through an action mechanism that destroys cell membranes of microorganisms.

As used herein, the term "dry eye syndrome" refers to an eye disease which leads to damage of the eye's surface, the eye's soreness, and irritating symptoms such as irritation, foreign body sensation, and dryness due to insufficient tears, excessive evaporation of tears, or an unbalance in the composition of tears, and tears and inflammation of the eye's surface (cornea and conjunctiva) rather than simple lack of tears cause discomfort of the eye, decreased vision, and unstability of a tear layer, and thus cause damage to the eye's surface, thereby increasing risk of the onset of pain, irregular corneal surface, blurred and fluctuated vision, corneal ulcers, and the like.

As used herein, the term "corneal opacity" refers to a state in which an opaque part is formed in the cornea, which is a normally transparent tissue, due to surface dryness, damage, inflammation, or the like, or the cornea is generally opaque.

DETAILED DESCRIPTION OF THE INVENTION

According to an aspect of the present invention, there is provided a pharmaceutical composition for treating and preventing dry eye syndrome, the composition containing, as an active ingredient, a peptide which has antibacterial activity and is composed of seven amino acids including an amino acid sequence selected from the group consisting of the following:

BOBWRYm, wherein, B is a basic amino acid each optionally selected from the group consisting of lysine (K) or arginine (R), and O is an aromatic amino acid each optionally selected from the group consisting of phenylalanine (F) or tryptophan (W).

In the pharmaceutical composition, the dry eye syndrome may be aqueous deficiency or evaporative dry eye. In this case, the aqueous deficiency dry eye is caused by lack of tears secreted from the lacrimal gland, and the evaporative dry eye is caused by excessive loss of moisture from the exposed surface of eye in the presence of the secretory function of the lacrimal gland. In addition, an octanoyl group may be added to the N-terminus of the peptide or an amine group to the C-terminus.

According to another aspect of the present invention, there is provided a pharmaceutical composition for treating keratoconjunctivitis, the composition containing, as an active ingredient, a peptide which has antibacterial activity and is composed of seven amino acids including an amino acid sequence selected from the group consisting of the following:

BOBWRYm, wherein, B is a basic amino acid each optionally selected from the group consisting of lysine (K) or arginine (R), and O is an aromatic amino acid each optionally selected from the group consisting of phenylalanine (F) or tryptophan (W).

According to another an aspect of the present invention, there is provided a pharmaceutical composition for alleviating corneal damage and corneal opacity, the composition containing, as an active ingredient, a peptide which has antibacterial activity and is composed of seven amino acids including an amino acid sequence selected from the group consisting of the following:

BOBWRYm, wherein, B is a basic amino acid each optionally selected from the group consisting of lysine (K) or arginine (R), and O is an aromatic amino acid each optionally selected from the group consisting of phenylalanine (F) or tryptophan (W).

In the pharmaceutical composition, the corneal damage and opacity may be caused by dry eye syndrome or keratoconjunctivitis, and the pharmaceutical composition may have a formulation selected from the group consisting of ointments, external skin preparations, aerosols, sprays, eye drops, oral preparations, and injections.

According to another aspect of the present invention, there is provided a method for treating dry eye syndrome in a subject, the method comprising administering the composition to the subject suffering from dry eye syndrome.

According to another aspect of the present invention, there is provided a use, in the production of a therapeutic agent for dry eye syndrome, of a peptide which has antibacterial activity and is composed of seven amino acids including an amino acid sequence selected from the group consisting of the following:

BOBWRYm, wherein, B is a basic amino acid each optionally selected from the group consisting of lysine (K) or arginine (R), and O is an aromatic amino acid each optionally selected from the group consisting of phenylalanine (F) or tryptophan (W).

The pharmaceutical composition according to the present invention may further include a pharmaceutically acceptable carrier or additive. As used herein, the term "pharmaceutically acceptable" means a substance that is physiologically acceptable and typically does not cause an allergic response such as gastrointestinal disturbance and dizziness, or a similar response when administered to humans. Examples of the additive may include an excipient, a disintegrant, a binder, a lubricant, a wetting agent, a dispersant, a stabilizer, and the like. Examples of the excipient may include lactose, mannitol, isomalt, microcrystalline cellulose, silicified microcrystalline cellulose, powdered cellulose, and the like. Examples of the disintegrant may include low-substituted hydroxypropylcellulose, crospovidone, sodium starch glycolate, croscarmellose sodium, starch, and the like. Examples of the binder may include hydroxypropyl cellulose, hypromellose, povidone, copovidone, pregelatinized starch, and the like. Examples of the lubricant may include stearic acid, magnesium stearate, sodium stearyl fumarate, and the like. Examples of the wetting agent may include polyoxyethylene sorbitan fatty acid ester derivatives, poloxamers, and polyoxyethylene castor oil derivatives. Examples of the dispersant may include hypromellose, hydroxypropyl cellulose, povidone, copovidone, sodium carboxymethylcellulose, methylcellulose, and the like. Examples of the stabilizer may include citric acid, fumaric acid, succinic acid, and the like. In addition, the pharmaceutical composition of the present invention may further include an anti-coagulant, a fragrance, an emulsifier, a preservative, and the like.

Furthermore, the pharmaceutical composition of the present invention may be formulated using methods known in the art in order to provide rapid, sustained, or delayed release of the active ingredient after administered to a mammal. The pharmaceutical formulation may be powder, granule, tablet, suspension, emulsion, syrup, aerosol, or soft or hard gelatin capsule.

As used herein, the term "treatment" refers to all actions that can relieve or beneficially change the symptoms of dry eye syndrome by administering the composition of the present invention.

The route of administration of the pharmaceutical composition may include oral, intravenous, intramuscular, intraarterial, transdermal, subcutaneous, intraperitoneal, intranasal, intestinal, topical, sublingual, or rectum, and the pharmaceutical composition may be applied, for example, by a topical application method. A parenteral administration includes subcutaneous, intradermal, intravenous, intramuscular, intralesional injection or infusion techniques.

The pharmaceutical composition of the present invention may be administered in a pharmaceutically effective amount. As used herein, the "pharmaceutically effective amount" refers to an amount sufficient to treat a disease at a reasonable benefit/risk ratio applicable to any medical treatment, and the effective dose level of the composition may be determined according to the factors including a type of individual and severity, an age, a sex of individual, a type of disease, an activity of drug, a sensitivity to drug, an administration time, an administration route and an excretion rate, duration of treatment, drugs used in combination with the composition, and other factors well known in the medical field. The composition of the present invention may be administered as a subject therapeutic agent or in combination with other therapeutic agents, and may be administered sequentially or simultaneously with a conventional therapeutic agent. In addition, the composition may be administered in single or multiple doses. Taking all of the above factors into consideration, it is important to administer an amount in which the maximum effect can be obtained in a minimal amount without side effects, and such an amount may be easily determined by a person skilled in the art.

The dosage of the pharmaceutical composition may vary according to various factors including the age, weight, general health, sex, administration time, administration route, excretion rate, drug combination, and severity of a specific disease of the subject. In addition, the pharmaceutical composition of the present invention may be used alone or in combination with methods using surgery, radiation therapy, hormone therapy, chemical therapy, and biological response modulators. In addition, the pharmaceutical composition may be administered at a dose within a range of 0.001 mg/kg to 200 mg/kg based on an adult, and when the pharmaceutical composition is an external preparation, it is preferable to apply the pharmaceutical composition at an amount of 1.0 mL to 3.0 mL based on an adult once daily to five times daily and continue for at least one month, but the dose is not limited to the scope of the present invention.

The present inventors have synthesized modified peptides in which various lipid components, such as palmitoyl group and octanoyl group, are attached to the N-terminus of the peptide in order to further increase the antibacterial activity and permeability based on the peptide found through the conventional basic screening to exhibit a high antibacterial action and immunomodulatory activity, and thus have developed a novel antibacterial and immunomodulatory peptide (hereinafter, abbreviated as "Peptide I") effective in treating immune diseases such as atopic dermatitis and diseases caused by pathogenic bacterial infection (Korean Patent No. 1855170). However, as a result of applying the peptide to a dry eye syndrome induced animal model, the inventors have confirmed a remarkable effect of alleviating corneal damage and corneal opacity compared to a control group, thereby completing the present invention.

Hereinafter, the present invention will be described in more detail with reference to Examples. The present invention may, however, be embodied in different forms and should not be construed as limited to the embodiments set forth herein. Rather, these embodiments are provided so that this disclosure will be thorough and complete, and will fully convey the scope of the present invention to those skilled in the art.

Example 1: Immunoregulation and Preparation of Antibacterial Peptide

The present inventors have developed a peptide (KFKWRYm) having an immunomodulatory function and an antibacterial activity through a conventional basic screening search, and have secured the patent for this (Korean Patent No. 10-1855170). Then, in order to develop an improved peptide having better immune regulation and antibacterial activity than the above-mentioned peptide, various variants are devised in the amino acid sequence of the patented peptide, and these are synthesized using a typical amino acid synthesis (Umbarger, H. E., *Ann. Rev. Biochem.,* 47: 533-606, 1978), and these were used as immunomodulatory and antibacterial candidate peptides. In addition, the present inventors have added an octanoyl group, an acetyl group, or the like to the N-terminus of the synthesized peptides as described above and/or modified a form in which an amine group was substituted instead of the carboxyl group of the C-terminus.

Example 2: Experiments of FPR2 Activation and Antibacterial Activity of Novel Peptide The present inventors have observed changes in calcium ion permeability in order to confirm whether or not the immunomodulatory and antibacterial peptide candidates of the present invention activates the immunomodulatory function of a living organism. Specifically, the concentration of calcium ions in cells was measured in order to confirm whether the peptide activates FPR2. To this end, the present inventors used RBL cells in which FPR2 was not expressed, RBL cells in which FPR1 was overexpressed (FPR1-RBL), and RBL cells in which FPR2 was overexpressed, and used Fura-2/AM, a staining material having a strong binding affinity for calcium, in a method for sensitively measuring free intracellular calcium ions. That is, the cells were cultured in RPMI medium containing 10% fetal bovine serum, centrifuged in the mid-log phase (1-3×$10^7$ cells/mL), and harvested. Then, the cells were washed several times with RPMI medium containing no fetal bovine serum and resuspended in RPMI medium to a concentration of 1×$10^7$ cells/mL. Then, the Fura-2/AM at a final concentration of 3 μM was added thereto and incubated in an incubator (37° C., 5% $CO_2$) for 45 minutes with continuous stirring. After the appropriate time elapsed, the cells were harvested and washed again several times with RPMI medium. Then, the cells were suspended in an appropriate amount of RPMI medium, in which sulfinpyrazone was supplemented at a concentration of 250 μM, so as to prevent the Fura-2 that entered into the cells from being released to the outside of the cells. Approximately 2×$10^6$ cells were taken each time and harvested by rapid centrifugation and resuspended in 1 mL of Locke solution in which EGTA was added but no calcium ions were added, and the absorbance ratios at two wavelengths of 340 nm and 380 nm were monitored on a spectrophotometer. After treating with the peptide according to the present invention at different concentrations (1 μM, 0.1 μM, and 0.01 μM) at intervals of about 1 minute, the difference in absorbance at two wavelengths was examined and this was later converted to the concentration of calcium ions freed into the cells according to the method of Grynkiewicz.

In addition, in order to measure the antibacterial activity of the peptide, *Staphylococcus aureus*, which is a gram-positive bacterium, and *Pseudomonas aeruginosa*, which is a gram-negative bacterium, were prepared, followed by 4th smearing on a flat medium of an agar, and culturing was performed overnight in a 36° C. incubator. The next day, strain colonies generated on the agar plate medium were inoculated into 3 mL-nutrient broth and cultured overnight in a shaking incubator at 36° C. and 220 rpm. The next day, the bacteria were diluted to measure absorbance at 600 nm, the absorbance was adjusted to 0.5, and the bacteria were diluted in a nutrient broth at a ratio of 1:100. Then, the peptides prepared in the Example were sequentially diluted in a nutrient broth at concentrations of 0, 1.25, 2.5, 5, 10, 20, and 40 μM, prepared 1 mL each, and then 1 mL of the diluted bacteria was inoculated. Then, the mixture was stirred at 36° C. and 220 rpm and incubated for 18 hours, and then the absorbance was measured at 600 nm.

As a result, most peptides exhibited FPR2 activation effect, and exhibited high antibacterial activity against *P. aeruginosa* and *S. aureus* (Table 1). The results of FPR2 activation and antibacterial activity of the peptide are summarized in Table 1 below.

TABLE 1

FPR2 Activation and Antibacterial Activity of Antibacterial Peptide

| SEQ ID | | FPR2 Activity | Antibacterial activity ($IC_{50}$, uM) | |
|---|---|---|---|---|
| NO. | Amino acid sequence | $EC_{50}$ (nM) | *P. aeruginosa* | *S. aureus* |
| 2 | Oct-KFKWRYm-$NH_2$ | 92.86 | 4.69 | 21.04 |
| 3 | KFKWRYm-$NH_2$ | 65.38 | 7.41 | 19.76 |
| 4 | Oct-KWKWRYm-$NH_2$ | 108.30 | 8.48 | 12.31 |
| 5 | Oct-RWRWRYm-$NH_2$ | 90.68 | 25.37 | 4.86 |
| 6 | RWRWRYm-$NH_2$ | 30.31 | 6.43 | 39.94 |

Example 3: Animal Model Construction

The present inventors prepared a mouse animal model to confirm the dry eye and inflammation alleviation efficacy of the peptide of the present invention, Peptide I (SEQ ID NO: 2). Specifically, 12-week-old male mice of the C57BL/6 family were used as the experimental animals, and 0.2% benzalkonium chloride was instilled to the eyes of mice, except for a control group that did not induce dry eye, twice daily for 15 days of the experiment period to induce dry eye and keratoconjunctivitis. Thereafter, the degree of corneal damage of the mice was evaluated through corneal staining on day 3, and experimental groups were classified through a randomized block design after selecting the mice with sufficient corneal damage. Subsequently, 1 hour after 0.2% benzalkonium chloride was administered from day 4, the Peptide I of the present invention (0.005% and 0.01%) was instilled to the eyes at twice daily intervals. Peptide I was dissolved in a saline solution according to the concentration of the administered solution, and the Restasis (0.05% cyclosporin) of Allergan Co., Ltd., which is being commercialized as a positive control group, and the saline solution was administered as a negative control group.

Example 4: Effect of Alleviating Corneal Damage

The present inventors examined the effects of treating dry eye and keratoconjunctivitis according to the administration of Peptide I of the present invention. Specifically, the mice were subjected to inhalation anesthesia with isoflurane on days 3, 7, 11, and 15 (days 0, 4, 8, and 12 of drug administration) of dry eye induction, and then the fluorescein, which is a fluorescece dye, was instilled to the eyes of the mice, and corneal staining was performed. Then, the residual fluorescein was washed with a saline solution, the eyeball was photographed with a fluorescent microscope to obtain an image, and the fluorescent-stained area was calculated and quantified using an image analysis program (Image J) to evaluate the degree of corneal damage due to dry eye and keratitis.

Figure 2:
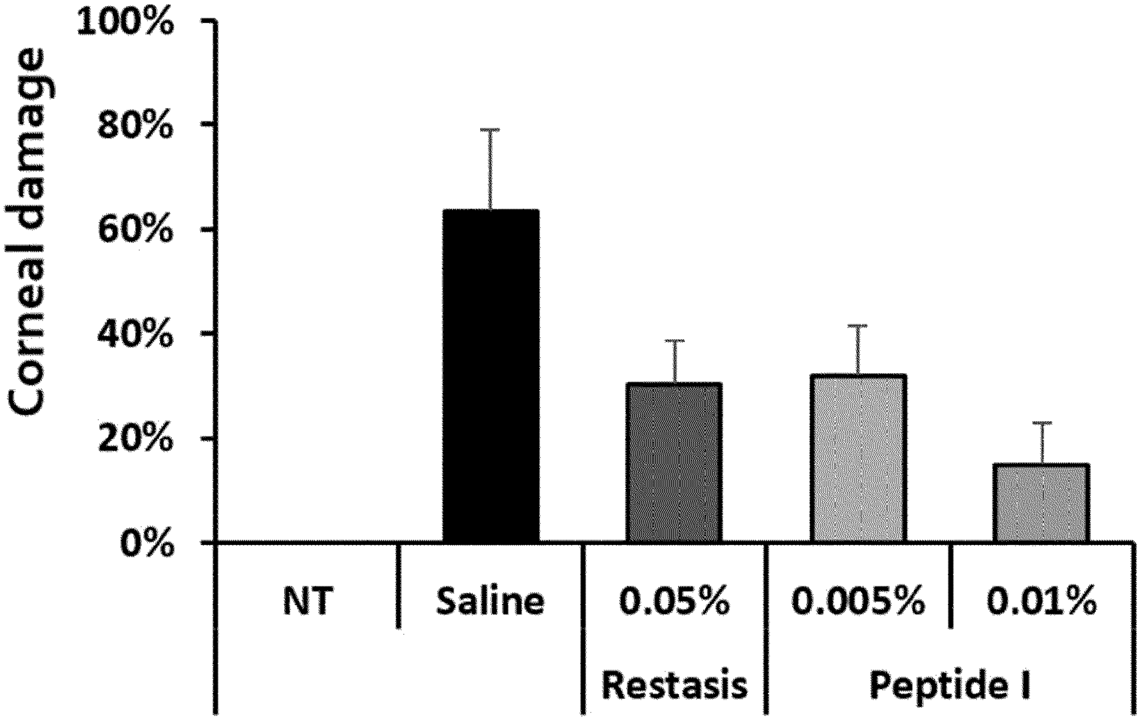
FIG. 2 is a graph obtained by quantifying and analyzing corneal damage according to the treatment of the peptide of the present invention.

As a result, it was found that administration of Peptide I of the present invention significantly alleviated corneal damage at lower concentrations compared to the control group (FIGS. 1 and 2).

Example 5: Effect of Alleviating Corneal Opacity

The present inventors examined the effects of alleviating corneal opacity according to the administration of Peptide I of the present invention. Specifically, the mice were subjected to inhalation anesthesia with isoflurane on days 3, 7, 11, and 15 (days 0, 4, 8, and 12 of drug administration) of dry eye induction, and then the eyeball was photographed with a microscope to obtain an image. The degree of corneal opacity was quantified and evaluated by scoring from 0 to 4 points, 0 points if the iris is clearly visible without opacity, 1 point if partially weak opacity is confirmed, 2 points if partial opacity or overall weak opacity is confirmed, 3 points if opacity is confirmed throughout the cornea, and 4 points if severe opacity and vascular development are observed.

Figure 3:
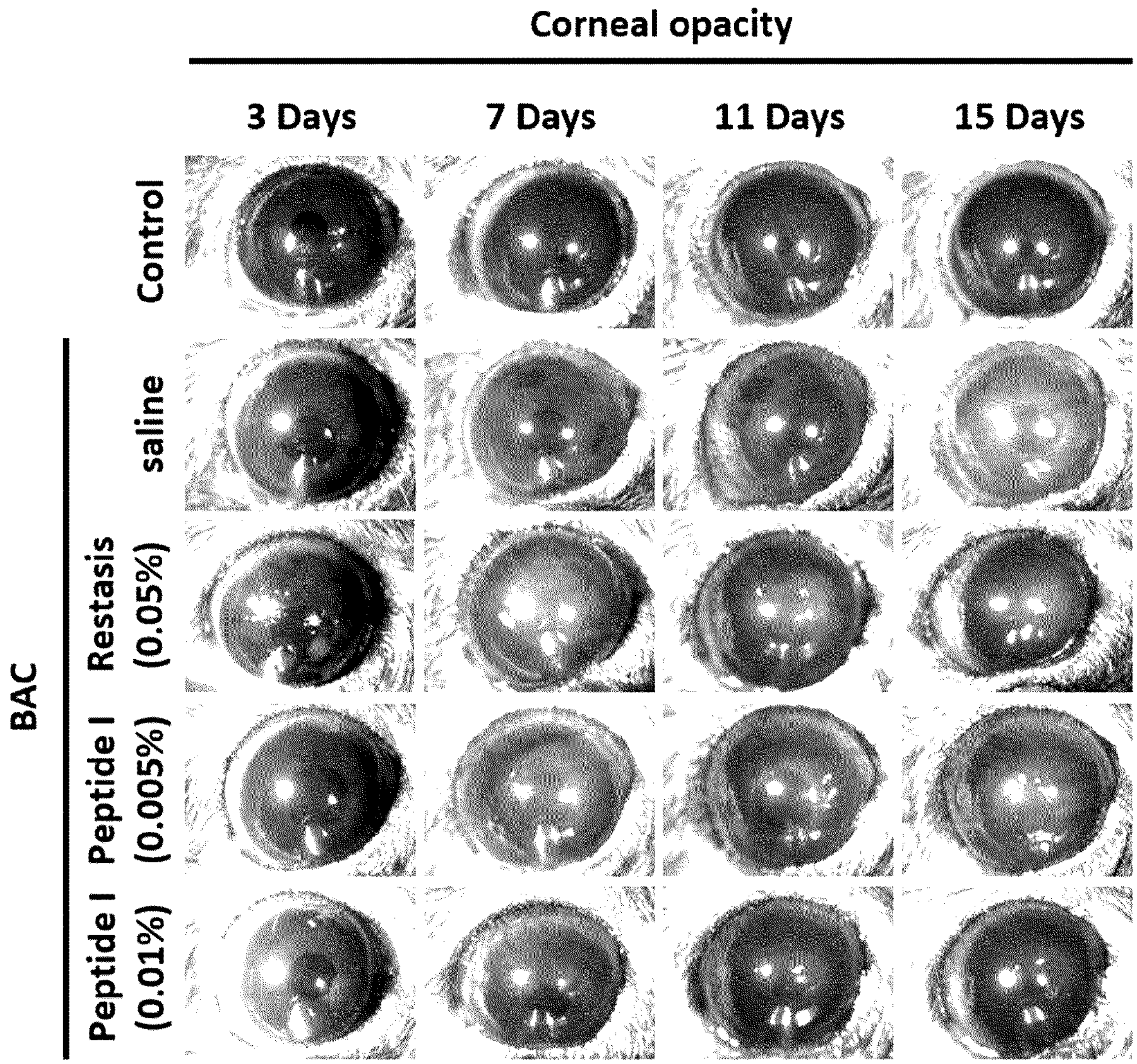
FIG. 3 shows images taken through a microscope of corneal opacity by treating the peptide of the present invention to mouse models.
Figure 4:
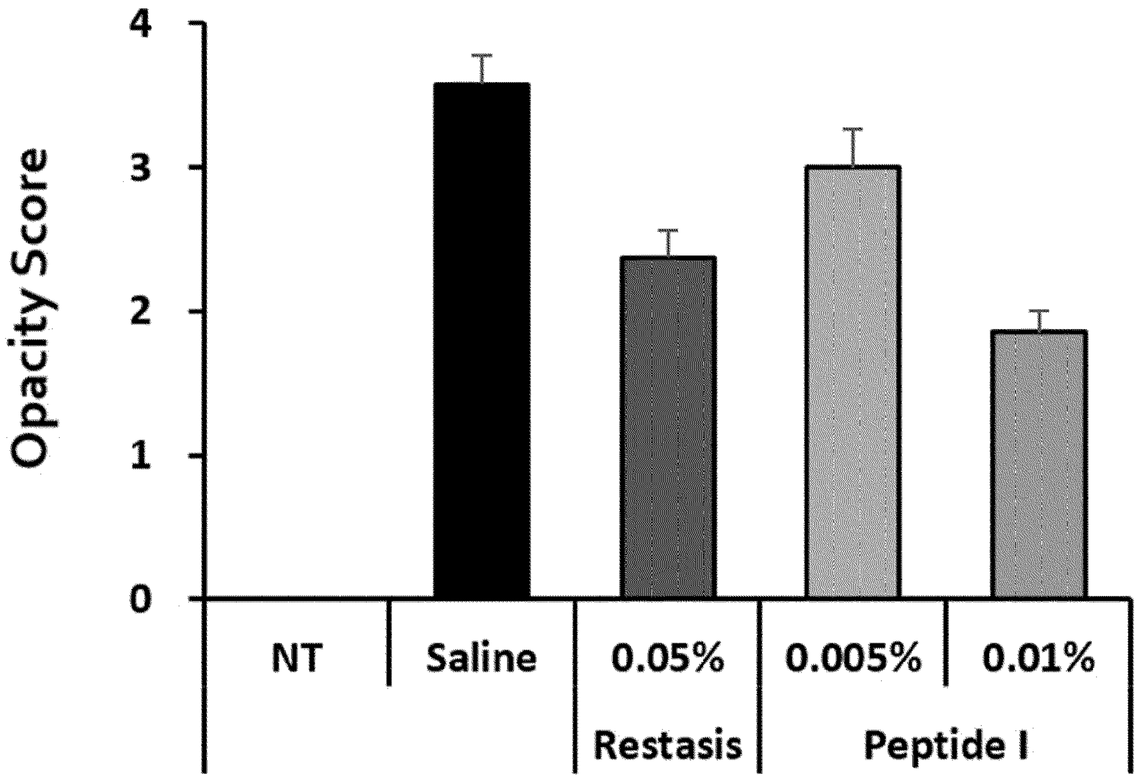
FIG. 4 is a graph obtained by quantifying and analyzing corneal opacity according to the treatment of the peptide of the present invention.

As a result, it was found that the administration of Peptide I of the present invention significantly alleviated corneal opacity at lower concentrations compared to the control group (FIGS. 3 and 4).

Consequently, as a result of administering the novel pharmaceutical composition for treating dry eye syndrome of the present invention to a mouse animal model, corneal damage and corneal opacity are significantly alleviated without side effects as compared to a control group, and thus the composition can be used as a material for effectively treating dry eye syndrome by restoring damaged corneas and increasing tear secretion.

The present invention is described with reference to the described examples, but the examples are merely illustrative. Therefore, it will be understood by those skilled in the art that various modifications and other equivalent embodiments can be made from the described embodiments. Hence, the real protective scope of the present invention shall be determined by the technical scope of the accompanying claims.

The invention claimed is:

1. A method for treating dry eye syndrome in a subject, comprising administering to the subject a therapeutically effective amount of a pharmaceutical composition including a peptide consisting of amino acid sequence of SEQ ID NO:2 as an active ingredient.

2. The method of claim 1, wherein an octanoyl group is added to the N-terminus of the peptide and/or an amine group is added to the C-terminus thereof.

3. The method of claim 1, wherein the dry eye syndrome is aqueous deficiency or evaporative dry eye.

4. The method of claim 1, wherein the pharmaceutical composition is a formulation of an ointment, external skin preparation, aerosol, spray, eye drop, oral preparation, or injection.

5. A method for treating keratoconjunctivitis in an individual, comprising administering to the subject a therapeutically effective amount of a pharmaceutical composition including a peptide consisting of the amino acid sequence of SEQ ID NO:2 as an active ingredient.

6. The method of claim 5, wherein an octanoyl group is added to the N-terminus of the peptide and/or an amine group is added to the C-terminus thereof.

7. The method of claim 5, wherein the pharmaceutical composition is a formulation of an ointment, external skin preparation, aerosol, spray, eye drop, oral preparation, or injection.

8. A method for alleviating corneal damage and corneal opacity, comprising administering to the subject a therapeutically effective amount of a pharmaceutical composition including a peptide consisting of the amino acid sequence of SEQ ID NO:2 as an active ingredient, wherein the corneal damage and corneal opacity is caused by dry eye syndrome or keratoconjunctivitis.

9. The method of claim 8, wherein the pharmaceutical composition is a formulation of an ointment, external skin preparation, aerosol, spray, eye drop, oral preparation, or injection.

* * * * *

SEQUENCE LISTING

```
<160> NUMBER OF SEQ ID NOS: 6

<210> SEQ ID NO 1
<211> LENGTH: 7
<212> TYPE: PRT
<213> ORGANISM: Artificial Sequence
<220> FEATURE:
<223> OTHER INFORMATION: anitimicrobial peptide
<220> FEATURE:
<221> NAME/KEY: VARIANT
<222> LOCATION: (1)
<223> OTHER INFORMATION: Xaa is Lys or Arg.
<220> FEATURE:
<221> NAME/KEY: VARIANT
<222> LOCATION: (2)
<223> OTHER INFORMATION: Xaa is Phe or Trp.
<220> FEATURE:
<221> NAME/KEY: VARIANT
<222> LOCATION: (3)
<223> OTHER INFORMATION: Xaa is Lys or Arg.
<220> FEATURE:
<221> NAME/KEY: VARIANT
<222> LOCATION: (7)
<223> OTHER INFORMATION: D-form amino acid

<400> SEQUENCE: 1

Xaa Xaa Xaa Trp Arg Tyr Met
1               5


<210> SEQ ID NO 2
<211> LENGTH: 7
<212> TYPE: PRT
<213> ORGANISM: Artificial Sequence
<220> FEATURE:
<223> OTHER INFORMATION: anitimicrobial peptide
<220> FEATURE:
<221> NAME/KEY: VARIANT
<222> LOCATION: (1)
<223> OTHER INFORMATION: Octanoyl group is added to the N-terminal
<220> FEATURE:
<221> NAME/KEY: VARIANT
<222> LOCATION: (7)
<223> OTHER INFORMATION: D-form amino acid
<220> FEATURE:
<221> NAME/KEY: VARIANT
```

<222> LOCATION: (7)
<223> OTHER INFORMATION: C term amidated.

<400> SEQUENCE: 2

Lys Phe Lys Trp Arg Tyr Met
1 5

<210> SEQ ID NO 3
<211> LENGTH: 7
<212> TYPE: PRT
<213> ORGANISM: Artificial Sequence
<220> FEATURE:
<223> OTHER INFORMATION: anitimicrobial peptide
<220> FEATURE:
<221> NAME/KEY: VARIANT
<222> LOCATION: (7)
<223> OTHER INFORMATION: D-form amino acid
<220> FEATURE:
<221> NAME/KEY: VARIANT
<222> LOCATION: (7)
<223> OTHER INFORMATION: C term amidated.

<400> SEQUENCE: 3

Lys Phe Lys Trp Arg Tyr Met
1 5

<210> SEQ ID NO 4
<211> LENGTH: 7
<212> TYPE: PRT
<213> ORGANISM: Artificial Sequence
<220> FEATURE:
<223> OTHER INFORMATION: anitimicrobial peptide
<220> FEATURE:
<221> NAME/KEY: VARIANT
<222> LOCATION: (1)
<223> OTHER INFORMATION: Octanoyl group is added to the N-terminal
<220> FEATURE:
<221> NAME/KEY: VARIANT
<222> LOCATION: (7)
<223> OTHER INFORMATION: D-form amino acid
<220> FEATURE:
<221> NAME/KEY: VARIANT
<222> LOCATION: (7)
<223> OTHER INFORMATION: C term amidated.

<400> SEQUENCE: 4

Lys Trp Lys Trp Arg Tyr Met
1 5

<210> SEQ ID NO 5
<211> LENGTH: 7
<212> TYPE: PRT
<213> ORGANISM: Artificial Sequence
<220> FEATURE:
<223> OTHER INFORMATION: anitimicrobial peptide
<220> FEATURE:
<221> NAME/KEY: VARIANT
<222> LOCATION: (1)
<223> OTHER INFORMATION: Octanoyl group is added to the N-terminal
<220> FEATURE:
<221> NAME/KEY: VARIANT
<222> LOCATION: (7)
<223> OTHER INFORMATION: D-form amino acid
<220> FEATURE:
<221> NAME/KEY: VARIANT
<222> LOCATION: (7)
<223> OTHER INFORMATION: C term amidated.

<400> SEQUENCE: 5

Arg Trp Arg Trp Arg Tyr Met
1 5

-continued

```
<210> SEQ ID NO 6
<211> LENGTH: 7
<212> TYPE: PRT
<213> ORGANISM: Artificial Sequence
<220> FEATURE:
<223> OTHER INFORMATION: anitimicrobial peptide
<220> FEATURE:
<221> NAME/KEY: VARIANT
<222> LOCATION: (7)
<223> OTHER INFORMATION: D-form amino acid
<220> FEATURE:
<221> NAME/KEY: VARIANT
<222> LOCATION: (7)
<223> OTHER INFORMATION: C term amidated.

<400> SEQUENCE: 6

Arg Trp Arg Trp Arg Tyr Met
1               5
```